(12) United States Patent
Younes

(10) Patent No.: US 6,758,217 B1
(45) Date of Patent: Jul. 6, 2004

(54) CONTROL OF AIRWAY PRESSURE DURING MECHANICAL VENTILATION

(75) Inventor: Magdy Younes, Winnipeg (CA)

(73) Assignee: University of Manitoba, Winnipeg (CA)

( * ) Notice: Subject to any disclaimer, the term of this patent is extended or adjusted under 35 U.S.C. 154(b) by 547 days.

(21) Appl. No.: 08/786,957

(22) Filed: Jan. 23, 1997

Related U.S. Application Data

(60) Continuation of application No. 08/433,645, filed on May 4, 1995, now abandoned, which is a division of application No. 08/191,916, filed on Feb. 4, 1994, now Pat. No. 5,507,282.

(30) Foreign Application Priority Data

Feb. 5, 1993 (GB) ............................................. 9302291

(51) Int. Cl.[7] ......................................... A61M 16/00
(52) U.S. Cl. ............................ 128/207.15; 128/207.14; 128/205.23
(58) Field of Search ...................... 128/200.26, 207.14, 128/207.15, 205.23, 671, 673, 692, 748

(56) References Cited

U.S. PATENT DOCUMENTS

| | | | | | |
|---|---|---|---|---|---|
| 3,893,451 | A | * | 7/1975 | Durard et al. | 128/673 |
| 4,214,593 | A | * | 7/1980 | Imbruce et al. | 128/748 |
| 4,383,534 | A | * | 5/1983 | Peters | 128/671 |
| 4,584,998 | A | * | 4/1986 | McGrail | 128/207.15 |
| 4,607,643 | A | * | 8/1986 | Bell et al. | 128/207.15 |
| 4,621,646 | A | * | 11/1986 | Bryant | 128/692 |
| 4,672,974 | A | * | 6/1987 | Lee | 128/673 |
| 4,813,431 | A | * | 3/1989 | Brown | 128/207.15 |
| 4,850,371 | A | * | 7/1989 | Broadhurst et al. | 128/207.15 |
| 4,872,483 | A | * | 10/1989 | Shah | 128/207.15 |
| 4,976,261 | A | * | 12/1990 | Gluck et al. | 128/207.15 |
| 5,218,970 | A | * | 6/1993 | Turnbull et al. | 128/748 |
| 5,290,231 | A | * | 3/1994 | Marcadis et al. | 128/673 |
| 5,361,753 | A | * | 11/1994 | Pothmann et al. | 128/748 |
| 5,398,692 | A | * | 3/1995 | Hickey | 128/673 |
| 5,564,425 | A | * | 10/1996 | Tonokura | 128/673 |

* cited by examiner

*Primary Examiner*—Aaron J. Lewis
(74) *Attorney, Agent, or Firm*—Sim & McBurney

(57) ABSTRACT

A endotracheal tube for patient ventilation is modified to permit measurement of pressure at the patient trachea by providing a chamber in the end of the ET tube to be located in the patient, airway. This chamber has a highly pliant external wall with a degree of redundancy and is connected to a pressure measuring device exterior of the patient by a lumen in the wall of the ET tube. In addition, apparatus for controlling airway pressure during exhalation comprises valve means connected via a first inlet to an exhalation tube from a patient airway, connected to a source of negative pressure through an outlet and having a second inlet with a variable flow control means for controlling the flow of gas therethrough. Gas pressure is controlled within the valve by varying the pressure gradient between the upstream and downstream sides of the second inlet so that it equals the pressure gradient between the patient airway and the downstream side of the second inlet.

8 Claims, 2 Drawing Sheets

CONTROL OF AIRWAY PRESSURE DURING MECHANICAL VENTILATION

"This isa divisionof application Ser. No. 08/191,916 field Feb. 4, 1994 now U.S. Pat. No. 5,507,282."

This application is a continuation, of application Ser. No. 08/433,645 filed May 4, 1995, now abandoned.

FIELD OF INVENTION

The present invention relates to modification to patient ventilators of a variety of different types to achieve improved operation.

BACKGROUND TO THE INVENTION

During mechanical ventilation the pressure at the external end of the endotracheal tube (ET tube) does not accurately reflect the pressure in the patient's trachea because the ET tube possesses a finite resistance which dictates the presence of a gradient between the two ends of the tube in the, presence of flow. During the inhalation phase the external pressure overestimates the pressure in the patient's trachea, the latter being the pressure actually applied to the patient to assist his breathing. In extreme cases, external pressure may be positive, implying that patient is being assisted, while tracheal pressure is negative, whereby the patient's breathing is actually being hindered, rather than assisted, on account of the resistance of the ET tube. Furthermore, because the external pressure during the inhalation phase is routinely used to make inferences about the mechanical properties of the patient's respiratory system, and hence disease progress, and since the external pressure during the inhalation phase includes a component used to overcome ET tube resistance, changes in ET tube resistance, as a result of secretions or kinking, may erroneously lead to the impression that patient's resistance has changed when in fact it has not.

Because during expiration flow is from patient to breathing circuit, external airway pressure (i.e. at the external end of the ET tube) underestimates the pressure in patient's trachea. When ET tube resistance is high, this difference can be significant and the patient may in fact be exhaling against a substantial positive pressure. This would not be detected when only external pressure is being monitored even though it may sufficiently impede expiration as to prevent the respiratory system from reaching its relaxation volume before the onset of the next inspiration (auto-PEEP). It is possible to estimate the pressure difference between the external and internal ends of the ET tube from the magnitude and direction of flow and the known pressure-flow characteristics of the ET tube used in the patient. This difference then can be added or subtracted, depending on direction of flow, from the externally measured pressure in order to obtain an estimate of tracheal pressure to be used for monitoring, estimation of patient's respiratory mechanics or for control of the ventilator. Such an approach has three important drawbacks:

1. It entails the use of flow measuring devices during both inspiration and expiration. Although monitoring inspiratory flow is not problematic and is available on many commercial ventilators, flow meters placed on the common tubing (i.e. between Y connector and ET tube) or the exhalation tubing are subject to water condensation and plugging by secretions which alter their calibrations.

2. Because the resistance of the ET tubes is not linear (i.e. resistance is flow dependent) and varies from size to size, complex electronic mechanisms are required to compute the estimated pressure difference along the ET tube and to subtract or add the difference to the measured external pressure.

3. Estimates of the pressure gradient along the ET tube must be carried out using the pressure-flow relation of the specific tube used. This relation is obtained from standard, clean tubes tested outside the patient. The pressure-flow relation so determined need not reflect the actual pressure-flow relation of the tube while in use. The resistance of the tube is situ is higher by a highly variable amount due to secretions and kinking (Marini, Amer. Rev. Resp. Dis. 140:10–16, 1989).

These problems can all be avoided by measuring the pressure directly at the tracheal end of the tube. At present, this can be done through the construction of home-made catheters and inserting them through improvised access sites in the external tubing. These catheters have to be individually constructed and sterilized and, because the catheter and its tip lie free in the lumen of the tube or in the trachea, they must be removed when suction is to be carried out. In addition, the tip of the catheter is subject to malfunction due to the accumulation of secretions. The free tip of the catheter is also liable to swing and flutter under the influence of the air currents, resulting in pressure artifacts.

As noted above, auto-PEEP is a recently-recognized complication in ventilated patients. With auto-PEEP the respiratory system fails to return to its relaxation volume prior to the onset of the next inhalation phase. Auto-PEEP may have serious consequences with respect to comfort, the respiratory muscles, and the circulation. In some patients, auto-PEEP develops because of an expiratory flow-limitation in the patient's own airway, which cannot be corrected by external devices. Most of the time, however, failure of proper emptying during exhalation is the result of high resistance of the tubing (including the endotracheal tube) and exhalation valve.

To avoid apparatus induced auto-PEEP, ideally airway pressure during exhalation should be controlled at zero (or at a constant positive pressure in the event external PEEP is desired) regardless of the rate of expiratory flow. There are currently no satisfactory means to control airway pressure in this fashion.

SUMMARY OF INVENTION

A modification to standard ET tubes is provided herein which permits the long term monitoring of pressure at the trachea and which eliminates many of the problems described above. Accordingly, in this aspect of the invention, there is provided an endotracheal tube for patient ventilation, comprising an elongate wall, a chamber formed in the wall adjacent the end to be located in the patient airway with the chamber having a highly pliant exterior wall, and a lumen formed in the wall extending from the chamber to a location remote from the chamber for connection thereat to pressure measuring apparatus. This arrangement permits the pressure in the patient trachea to be determined and monitored directly.

In addition, the present invention provides a solution to the auto-PEEP problem. Accordingly, another aspect of the present invention provides means for controlling airway pressure during exhalation at a predetermined value irrespective of the rate of expiratory flow. This aspect of the present invention, therefore, provides apparatus for controlling patient airway pressure during exhalation, comprising valve means having first inlet means for connecting to an exhalation tube from a patient airway, outlet means for connection to a source of negative pressure, and second inlet means having variable flow control means therein for controlling the flow of gas through the second inlet means; and means for controlling gas pressure within the valve means such that the gas pressure gradient between the upstream and downstream sides of the second inlet means is equal to the gas pressure gradient between the patient airway and the downstream side of the second inlet means. In this way, the airway pressure during exhalation is controlled at a predetermined value irrespective of the rate of expiratory flow.

DESCRIPTION OF PREFERRED EMBODIMENT

Figure 1A:
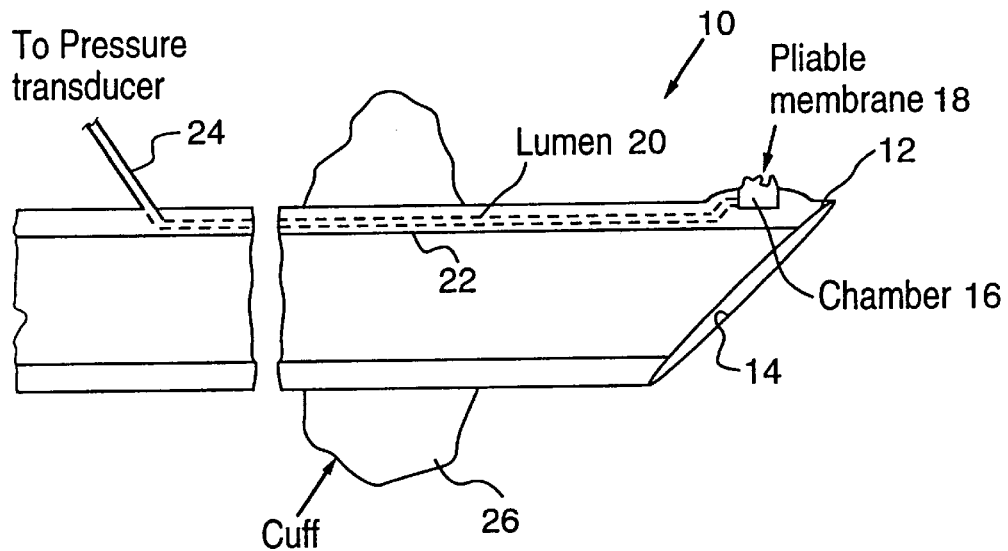
FIG. 1A is a part-sectional view of an endotracheal tube provided in accordance with the embodiment of the first aspect of the invention.
Figure 1B:
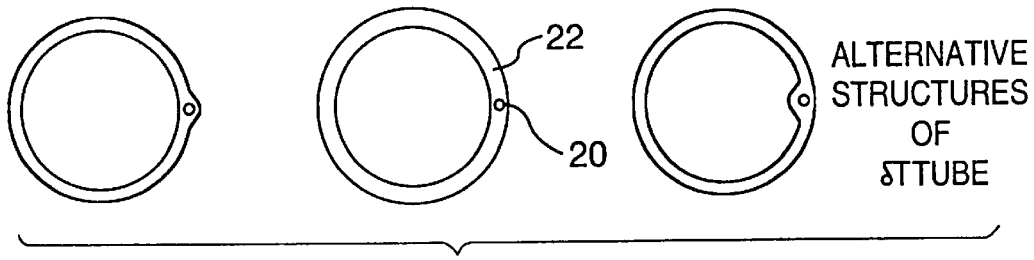
FIG. 1B contains three cross-section views, labelled I, II and III, of the endotracheal tube of FIG. 1A, illustrating three alternative structures.
Figure 1C:
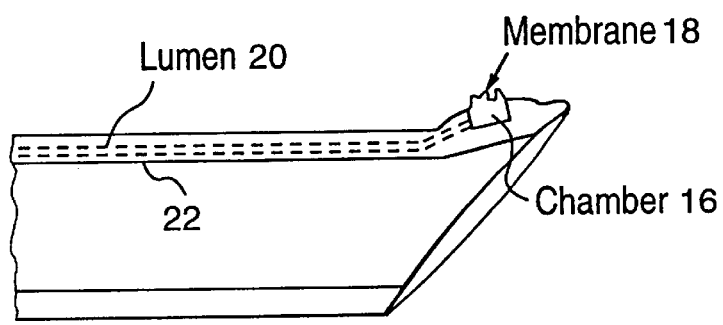
FIG. 1C is a close-up view of the downstream end of the endotracheal tube of FIG. 1A with a modified structure.

Referring first to FIGS. 1A to 1C, an endotracheal tube 10 is constructed such that the wall thickness near the long end 12 of the slanted orifice 14 is greater than usual in order to accommodate a small chamber 16. The external wall of the chamber is made of highly pliable membrane 18 with some redundancy such that, starting from a collapsed position (membrane 18 abutting on internal wall of chamber 16) about 0.1 ml or more of air can be injected in chamber without development of significant back pressure (e.g. less than about 1 cm $H_2O$). A lumen 20 incorporated in the wall 22 of the tube 10, communicates with the chamber 16 and runs along the tube 10 until near the external end where it connects with an external narrow tube or catheter 24 that serves as a conduit to the pressure measuring device (transducer). Three alternate locations for the lumen 20 within the wall 22 of the ET tube are shown in FIG. 1B.

In normal use, the pliable external wall 18 of the chamber 16 normally is kept from touching the wall of trachea through the action of the standard inflatable cuff 26 to be found on most commercially available ET tubes.

The tube 10 is inserted in the normal way into the patient airway and the cuff 26 is inflated. The lumen 20 connecting to the pressure chamber 16 also is connected via tube 24 to a pressure transducer with a small displacement volume through a 3-way stopcock or other appropriate connector. A small syringe is attached to the stopcock and air is withdrawn from the chamber until pressure is negative. Air then is injected until pressure returns to atmospheric when the ET tube is open to air and there is no flow (e.g. end of expiration). An additional amount of air then is injected to permit gas transfer from chamber 16 to transducer as a result of pressure fluctuations in trachea. The stopcock then is turned such that the chamber 16 is connected to the transducer but the syringe is disconnected. The ET tube then now is calibrated to effect pressure measurements.

The critical chamber volume with which there is no back-pressure ($V_{crit}$) depends on the volume of transducer and connecting tubing to be used. The smaller the latter volume (i.e. of transducer and tubing), the less gas needs to be transferred from chamber to transducer as a result of a given pressure change in trachea. This is highly advantageous as it reduces the requirement for a large $V_{crit}$ while enhancing the responsiveness of the entire measurement system.

In another preferred embodiment, the long side of the slanted end of the ET tube 10 is made to gently curve or flare outwards (see FIG. 1C) or modified in various ways. This may reduce the risk of secretions accumulating on top of the pliable membrane 18. An added benefit is the reduction of turbulence at the external surface of the pliable membrane.

In accordance with this first aspect of the invention, therefore, there is provided a novel design for an endotracheal tube which permits monitoring of the tracheal pressure directly. A small chamber is located within the wall of the tube near the tracheal end with one or more walls of this chamber comprising pliable, redundant material and a lumen, also located within the wall of the tube, connects the chamber to a catheter exiting the tube near its external end.

Specific features of this embodiment of the invention, which may be used alone or in combinations of two or more features, comprise the following:

Where the external catheter connected to the lumen is equipped with connectors for the purpose of connecting the catheter to pressure measuring devices and/or to syringes.

Where the tip of the endotracheal tube is additionally modified such that it gently curves outward.

Where the end of the endotracheal tube incorporates more than one chamber.

Figure 2:
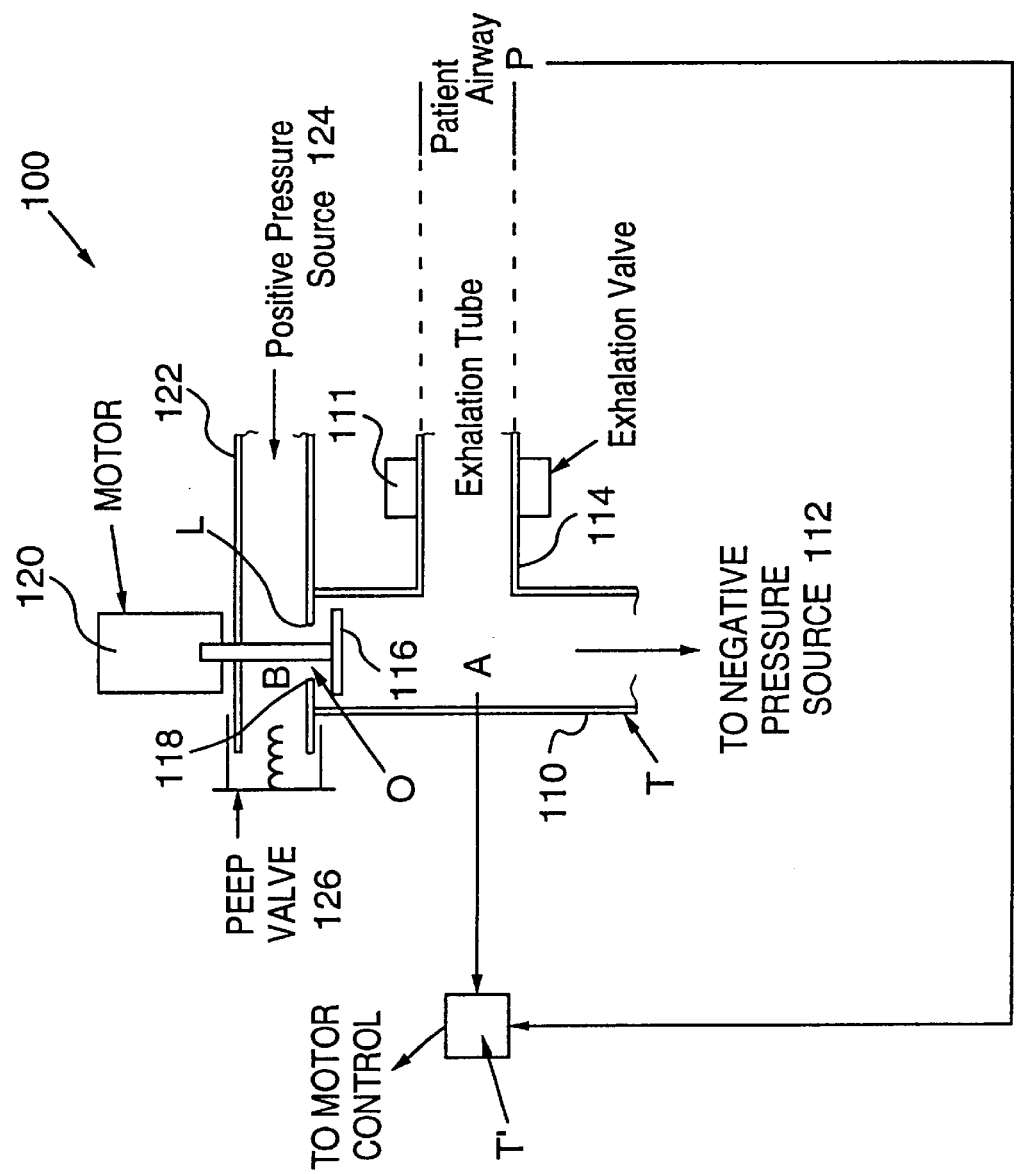
FIG. 2 illustrates an arrangement of valving in accordance with one embodiment of the second aspect of this invention.

Turning now to consideration of FIG. 2, there is illustrated therein one embodiment of a device 100 connected to the exhalation valve of a ventilator of any design and comprising a negative pressure source, an optional positive pressure source and a variable leak whose magnitude is continuously adjusted in response to changes in pressure at patient airway. As seen in FIG. 2, an exhalation tube 110 distal to the standard exhalation valve 111 is connected to a negative pressure source 112, which may be a wall suction outlet with appropriate threshold mechanism to control maximum negative pressure, the intake pipe of a blower or any other source of regulated negative pressure. For a given negative pressure source, the pressure at the junction between exhalation tube 114 and device 100 (point A) is a function of flow in the tubing 110 (T) connecting that junction to the negative pressure source 112 (less negative pressure at a higher flow). This flow is, in turn, partly derived from patient and partly from a variable leak (L). The magnitude of leak is varied through the to and from motion of a plate 116 or cone (not illustrated) relative to an inlet orifice 118 (O), as controlled by a motor 120. In one preferred embodiment, the position of the disc 116 at any moment is determined, on one hand by the gas pressure gradient it is subject to (pressure at point B in pipe 122 less pressure on the opposite side of the disc 116, point A) and, on the other hand, by a retractile force exerted on the disc 116 by the small motor 120 to which it is coupled.

It can be readily appreciated that the force exerted by the motor 120 determines the pressure gradient between points A and B, regardless of the absolute value of pressure at either site and regardless of flow from patient. Thus, for a given pressure at point B, and a given retractile force by the motor 120, if the patient flow decreases, the pressure at point A tends to become more negative (less flow through T). This, in turn increases the pressure gradient from B to A causing the disc 116, to move away from the motor 120, thereby reducing resistance and increasing flow from B to A to offset the decrease in patient flow. The disc 116 then moves until the pressure gradient between B and A just offsets the retractile force of the motor 120 which is set by the power supplied to the motor 120.

In another preferred embodiment, the position of the disc 116 is adjusted by a stepper motor, or other type of motor, that controls position as opposed to force, in order to maintain the pressure gradient between points B and A at a desired level.

The pressure at point B can be atmospheric (chamber upstream from leak (L) vented to room). In this case, pressure at point A can be regulated between a maximum value that is close to atmospheric pressure (disc 116 fully extended and leak is maximal) and a minimal value representing the maximum negative pressure that can be generated by the negative pressure source 112 (disc 116 fully retracted, and flow in L is zero). Alternatively, pressure at point B can be maintained at a constant positive value produced by gas flow from a positive pressure source 124 through a valve 126 with a threshold opening pressure (e.g. any of commercially available PEEP valves or equivalent mechanism). In this case, pressure at point A can be regulated between a maximal value represented by the positive pressure at point B and a minimal value, when the disc 116 is fully retracted, given by the most negative pressure available from the negative pressure source.

The pressure at patient's airway (point P) is measured continuously with a differential pressure transducer. Current is supplied to the motor 120 in such a way that the pressure gradient between B and A equals the gradient between P and A. In this fashion, pressure at the patient airway is controlled at the same level as at point B (i.e. atmospheric or constant positive pressure) regardless of the rate of expiratory flow and hence gradient between P and A.

Any of several standard electronic methods can be used to match the B to A pressure gradient to the P to A gradient. With one embodiment, the pressure gradient between P and A is measured with a differential transducer (T', FIG. 2) to produce an electrical signal corresponding in magnitude to the measurement and current is channeled to a linear force generating motor 120 in proportion to that electrical signal (FIG. 2). The proportionality of application of the electrical signal is determined by the size of disc 116 and characteristics of the motor 120. Alternatively, the pressure from P to B can be measured and the resulting error signal is used to servo-control the position of the disc 116 or the current applied to motor 120 depending on which kind of motor is used. As indicated earlier, any of many other standard electronic and microprocessor techniques can be used to effect this matching. Such techniques can also be utilized to cause pressure at point P to vary as a predetermined function of exhalation time as opposed to being constant throughout exhalation.

Airway pressure (P) ideally is sampled at the patient's own airway, for example, employing the device of FIG. 1. In this way, patient's own airway pressure, and not an external pressure, is regulated. If this is not practicable, P should be sampled as close as possible to the ET tube. In the latter case, some allowance must be made for the pressure gradient along the ET tube (i.e. between trachea and sampling point). Since both this gradient and the gradient between sampling point and point A are related to flow, such allowance may require only an adjustment of the gain of the signal from the differential pressure transducer measuring pressure gradient between P and A (T'). This adjustment varies with the size of ET tube used. If, however, the pressure-flow relation for tubing between P and A is substantially different, in the qualitative sense, from that of the ET tube, simple gain adjustment may not be adequate. An alternative approach in this case is to sum the output of the differential transducer (P–A) with another signal (S) which is a function of expiratory flow (S=fV̇), this function being. ET tube specific. The summed function then is used to control the motor 120.

Although independent positive and negative pressure sources can be used, an alternative embodiment consists of using a blower or fan as the source for both. In this case, a leak must be incorporated in the intake side of the blower, close to the blower itself. This ensures that some gas always flows through the PEEP valve 126, thereby maintaining pressure at point B, and hence at patient's airway, at the desired level at all time.

In accordance with the second aspect of the invention, therefore, there is provided a device for attachment to the exhalation tubing of a mechanically-ventilated patient to regulate pressure at the airway during exhalation. In one embodiment, the device comprises chamber or tubing which connects at one point to a patient exhalation tube, at another point to a negative pressure source and at a third point to a variable leak into the chamber or tubing; and means to alter the magnitude of the leak such that the pressure gradient between a point upstream from the leak and pressure in the chamber or tubing equals a desired value, the latter means comprising a disc, cone or similar structure whose position determines the magnitude of the leak, a motor which is coupled to the disc or cone and which, in response to appropriate electrical commands, alters the force applied to disc or cone, or the position of the disc or cone in a predictable manner, thereby changing the magnitude of the leak as desired, and electronic circuitry to provide the motor with power to cause disc or cone to move in such a way that pressure at patient airway matches pressure upstream from the leak.

Specific features of this embodiment of the invention, which may be used alone or in combinations of two or more features comprise the following:

When provided with means to cause pressure upstream from the leak to be above atmospheric (positive), particularly when the positive pressure is produced by continuous flow from a positive pressure source across a spring loaded valve or other valve with a critical opening pressure.

Where the source of negative and/or positive pressure are incorporated within the device.

Where a common blower is used to provide the source of both positive and negative pressures, particularly where an additional leak is introduced on the intake side of the blower.

Where pressure at patient airway is sampled from a site within the patient's trachea for the sake of estimating pressure gradient between patient airway and device.

Where the signal corresponding to pressure gradient between patient airway and device is made up of two components, one component corresponding to pressure gradient between a point in the tubing external to the patient and the device, the one component is measured, and a second component, which represents the pressure gradient between patient's own airway and the said external point of sampling, which is estimated, particularly where the estimated component of the pressure gradient is described by estimated pressure=$f\delta P$ where $\delta P$ is the pressure gradient between external sampling point and device and $f$ is a function describing the estimated relation between the pressure gradient from patient's own airway to external sampling site and δP, or particularly where the estimated component of the pressure gradient is described by estimated pressure=$f\dot{V}$ where $\dot{V}$ is flow along the exhalation tubing and $f$ is a function that is assumed to describe the pressure-flow relation in the tubing between patient's own airway and external sampling site.

SUMMARY OF DISCLOSURE

In summary of this disclosure, the present invention provides novel means for ensuring accurate pressure delivery from a ventilator to a patient. Modifications are possible within the scopes of this invention.

What I claim is:

1. An endotracheal tube for patient ventilation and for measuring airway pressure comprising:
    an elongate wall enclosing and defining an unobstructed elongate passage for delivery of ventilating gas through an open end thereof to a patient airway,
    a chamber formed in said elongate wall adjacent said open end of said elongate passage, said chamber having a highly pliant exterior wall which permits airway pressure to be transmitted directly to the chamber, and
    a lumen formed in said elongate wall extending from said chamber to a location remote from said chamber connected at such a remote location to a pressure measuring apparatus for measuring airway pressure determined by movement of the exterior wall of said chamber causing compression and decompression of gas in said chamber in response to changes in airway pressure and the presence of gas in the lumen.

2. The apparatus of claim 1 wherein said highly pliant exterior wall has a degree of redundancy permitting at least about 0.1 ml of air to be injected into the chamber without the development of significant backpressure.

3. The apparatus of claim 2 wherein said one end of said tube is flared outwardly.

4. The apparatus of claim 2 wherein said lumen is connected at its location remote from said chamber to a catheter for connection to the pressure-measuring apparatus.

5. The apparatus of claim 2 wherein said elongate wall is of uniform thickness.

6. The apparatus of claim 2 wherein said elongate wall has a ridge of increased thickness extending radially outwardly of a remainder of the elongate wall and said lumen is formed in said ridge.

7. The apparatus of claim 2 wherein said elongate wall has a ridge of increased thickness extending radially inwardly of a remainder of the elongate wall and said lumen is formed in said ridge.

8. The apparatus of claim 2 wherein more than one said chamber is incorporated in said elongate wall at said one end of the endotracheal tube.

* * * * *